United States Patent
Pannkuk (10) Patent No.: US 11,571,367 B2
(45) Date of Patent: Feb. 7, 2023

(54) COMPOSITION AND METHOD FOR ENDODONTIC DEBRIDEMENT

(71) Applicant: Terrell F. Pannkuk, Santa Barbara, CA (US)

(72) Inventor: Terrell F. Pannkuk, Santa Barbara, CA (US)

( * ) Notice: Subject to any disclaimer, the term of this patent is extended or adjusted under 35 U.S.C. 154(b) by 222 days.

(21) Appl. No.: 17/067,128

(22) Filed: Oct. 9, 2020

(65) Prior Publication Data
US 2021/0022964 A1 Jan. 28, 2021

Related U.S. Application Data

(63) Continuation-in-part of application No. 16/375,088, filed on Apr. 4, 2019, now Pat. No. 11,147,747.

(60) Provisional application No. 62/653,102, filed on Apr. 5, 2018.

(51) Int. Cl.
*A61C 5/40* (2017.01)
*A61K 6/60* (2020.01)
*A61C 5/50* (2017.01)

(52) U.S. Cl.
CPC .................. *A61K 6/60* (2020.01); *A61C 5/40* (2017.02); *A61C 5/50* (2017.02)

(58) Field of Classification Search
CPC .............. A61C 5/40; A61C 5/50; A61K 6/60
USPC ........................................................ 433/224
See application file for complete search history.

(56) References Cited

U.S. PATENT DOCUMENTS

| | | | | |
|---|---|---|---|---|
| 5,366,733 A | * | 11/1994 | Brizzolara | A61C 19/063 514/963 |
| 5,622,498 A | * | 4/1997 | Brizzolara | A61K 9/1647 433/80 |
| 5,674,074 A | * | 10/1997 | Angelo, Jr. | A61C 8/0006 433/215 |
| 5,756,361 A | * | 5/1998 | Winterbottom | G01N 33/52 436/811 |
| 6,409,764 B1 | * | 6/2002 | White | A61C 8/0006 623/23.72 |
| 9,050,332 B2 | * | 6/2015 | Haberlein | A61K 38/47 |
| 11,147,747 B2 | * | 10/2021 | Pannkuk | A61K 6/52 |
| 2008/0070194 A1 | | 3/2008 | Wagner et al. | |
| 2014/0356797 A1 | * | 12/2014 | Tsuji | A61K 6/58 433/1 |
| 2016/0100959 A1 | * | 4/2016 | Kim | A61L 2/0011 134/140 |
| 2017/0100464 A1 | * | 4/2017 | Dobboletta | A61C 19/063 |
| 2018/0138019 A1 | * | 5/2018 | Shindo | H05H 1/42 |
| 2019/0307651 A1 | * | 10/2019 | Pannkuk | A61K 6/52 |
| 2021/0022964 A1 | * | 1/2021 | Pannkuk | A61K 6/69 |
| 2021/0077223 A1 | * | 3/2021 | Mounir | A61C 5/30 |

OTHER PUBLICATIONS

Farouk et al., "Histological evaluation of the effect of trichloroacetic acid and mineral trioxide aggregate on human teeth pulp", Tanta Dental Journal, 2017, pp. 40-44, vol. 14.
Heithersay, "Invasive cervical resorption", Endodontic Topics, 2004, pp. 73-92, vol. 7.

(Continued)

*Primary Examiner* — Matthew M Nelson
(74) *Attorney, Agent, or Firm* — The Webb Law Firm (57) ABSTRACT

Provided herein are compositions and kits including trichloroacetic acid, and methods of using the same for debridement during endodontic treatment.

20 Claims, 8 Drawing Sheets

(56) References Cited

OTHER PUBLICATIONS

Karami et al., "Histological evaluation of the effect of three medicaments; trichloracetic acid, formocresol and mineral trioxide aggregate on pulpotomised teeth of dogs", Aust Endod J, 2009, pp. 18-28, vol. 35.
Register et al., "Accelerated Reattachment with Cementogenesis to Dentin, Demineralized in Situ, I Optimum Range", Accelerated Reattachment, 1975, pp. 646-655, vol. 46:11.
Yug et al., "Histologic Study of Depressed Acne Scars Treated with Serial High-Concentration (95%) Trichloroacetic Acid", Dermatol Surg, 2006, pp. 985-990, vol. 32.

\* cited by examiner

COMPOSITION AND METHOD FOR ENDODONTIC DEBRIDEMENT

CROSS-REFERENCE TO RELATED APPLICATIONS

The present application is a continuation-in-part of U.S. patent application Ser. No. 16/375,088, filed Apr. 4, 2019, and claims priority to U.S. Provisional Patent Application No. 62/653,102, filed Apr. 5, 2018, the contents of which are incorporated herein by reference in their entirety.

BACKGROUND OF THE INVENTION

Field of the Invention

Provided herein are composition, methods, and kits for endodontic debridement.

More particularly, provided herein are compositions and kits including trichloroacetic acid, and methods of using the same for performing debridement and/or pulpectomies associated with endodontic treatment.

Description of Related Art

It is well-established that the most challenging aspect of root canal treatment is complete debridement and clearing of debris and tissue from the root canal system following endodontic access. Known solutions are replete with shortcomings.

Sodium hypochlorite is the current "gold standard" solution for use in debridement during endodontic treatment. Sodium hypochlorite digests soft tissue and disinfects the surrounding area. However, the mechanism of action of sodium hypochlorite is incredibly slow, taking 10 or more minutes to dissolve dental pulp, even at a strength of 6.25%. In addition, sodium hypochlorite is viscous, limiting its ability to access fins, anastomoses, and accessory canals. Further, sodium hypochlorite is unable to dissolve exogenous materials from prior treatments that may be present within the root canal.

Like sodium hypochlorite, EDTA, chlorhexidine, and alcohol are similarly lacking in strength and ability to access all areas of the root canal to be effective.

Accordingly, there is a need in the art for an effective, yet safe, composition for use in debridement during endodontic treatment.

SUMMARY OF THE INVENTION

Provided herein is a method of dehydrating root canal pulp including the step of administering, to dental pulp within the mouth of a patient, a composition including trichloroacetic acid, the composition optionally including one or more buffers or excipients.

Also provided herein is a method of performing endodontic treatment, including the steps of performing endodontic access, performing coronal flaring, thereby opening one or more root canals and exposing dental pulp within the one or more canals, applying a composition comprising trichloroacetic acid to the exposed dental pulp, the composition optionally including one or more buffers or excipients, cleaning and shaping the one or more root canals, applying a composition including trichloroacetic acid, the composition optionally including one or more buffers or excipients, to the one or more cleaned and shaped root canals, flushing the one or more root canals with a first flushing solution, and drying the one or more root canals.

Also provided herein is a kit including a syringe having a barrel with a proximal end, a distal end, and a sidewall therebetween defining a reservoir and a longitudinal axis, a plunger received at least partially within the reservoir, and a metal needle tip attached to the distal end of the syringe barrel, wherein at least a portion of the needle tip is disposed at an angle relative to the longitudinal axis of the barrel, and a composition including trichloroacetic acid received within the reservoir.

DESCRIPTION OF THE INVENTION

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges (e.g., ±10%, 9%, 8%, 7%, 6%, 5%, 4%, 3%, 2%, 1%, or 0.5%) can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "patient" or "subject" refers to members of the animal kingdom including but not limited to, human beings and "mammal" refers to all mammals including, but not limited, to human beings.

As used herein, the "treatment" or "treating" of a wound or defect means administration to a patient by any suitable dosage regimen, procedure, and/or administration route an amount of a composition, device or structure effective to, and with the object of achieving a desirable clinical/medical end-point, including attracting progenitor cells, healing a wound, correcting a defect, etc.

As used herein, the terms "comprising," "comprise" or "comprised," and variations thereof, are open ended and do not exclude the presence of other elements not identified. In contrast, the term "consisting of" and variations thereof is intended to be closed and excludes additional elements in anything but trace amounts.

As used herein, "endodontic treatment", or "endodontic therapy", refers to the procedure commonly known as "root canal therapy." As used herein, "endodontic treatment" refers to one or more steps of removing pulp from the space inside of a tooth, cleaning, disinfecting, and shaping the root canal, and filling the space.

Provided herein are compositions and kits including trichloroacetic acid (TCA), and methods of using the same in endodontic treatment. The following disclosure will exemplify TCA, and, in particular, 90% TCA. However, those of skill in the art will appreciate that acids of a similar mass (e.g., a molar mass of ~160 g·mol$^{-1}$) and strength (e.g., a pK$_a$ of ~0.6) will be useful for debridement during endodontic treatment as described herein. In particular, as TCA is a derivative of acetic acid, other derivatives of acetic acid (e.g., chloroacetic acid, dichloroacetic acid, trifluoroacetic acid, and tribromoacetic acid) are expected to be similarly useful, as are other simple carboxylic acids (e.g., C1-C4 carboxylic acids). In some aspects, a composition as described herein can optionally, in non-limiting aspects, include one or more excipients or carriers. An excipient is an inactive substance used as a carrier for the active ingredients of a composition. Although "inactive," excipients may facilitate and aid in increasing the delivery, stability, or bioavailability of an active ingredient in a composition. Excipients include antiadherents, binders, rheology modifiers, coatings, emulsifiers, oils, buffers, salts, acids, bases, fillers, diluents, solvents, colorants, glidants, lubricants, preservatives, antioxidants, sorbents, vitamins, etc., as are available in the pharmaceutical/compounding arts (see, generally, Troy, D B, Editor, Remington: The Science and Practice of Pharmacy, 21st Ed., Lippincott Williams & Wilkins (2005) for a discussion of pharmaceutically-acceptable carriers and excipients). However, in other aspects, the composition consists essentially of, or consists only of, trichloracetic acid.

A composition as described herein can include, in some aspects, about 90% trichloracetic acid, including in some aspects 90% trichloracetic acid. However, in other aspects, the TCA is about 50%, about 60%, about 70%, about 80%, or about 100% TCA, all percentages and subranges therebetween inclusive.

Also, provided herein are kits including TCA and a mechanism or device for delivering TCA during endodontic treatment. In some aspects, the mechanism or device is a syringe, as is known in the art. Useful syringes can be formed of a glass or plastic barrel having a proximal end, a distal end, and a sidewall therebetween defining a reservoir for holding a composition (e.g., TCA as described herein). A mechanism or device useful for delivering TCA or other suitable acid, for example and without limitation a syringe, can be sized as appropriate. In non-limiting aspects, the device is of a similar size as an endodontic hand file (e.g., 21 mm-31 mm in length, all lengths and sub-ranges therebetween inclusive). As known in the art, syringes also include plungers for delivering a composition held within the reservoir through a needle arranged (via either permanent or reversible connections) at the distal end of the syringe. As is known in the art, plungers can be formed of any useful material, including plastic. Needles of any suitable gauge and length can be used in the kit of the present invention. In some aspects, the needle is a 30-gauge needle. In some aspects, the needle is about 10 mm to about 15 mm in length.

A device suitable for delivering TCA during endodontic treatment can be of any suitable shape or configuration to allow for precise delivery while minimizing accidental or extraneous delivery of TCA to tissues other than the target. For example, and without limitation, suitable devices can be angled (e.g., the barrel and/or the needle) to allow for precision delivery, to improve comfort, and/or to minimize fatigue during use. In such aspects, the syringe barrel can be suitably angled, the syringe needle can be suitably angled, or both. In other aspects, the syringe (barrel and/or needle) can be straight. In further non-limiting aspects, the syringe needle includes one or more side vents to control delivery and, for example and without limitation, to prevent gross apical extrusion, that is, extrusion of TCA beyond the area of treatment to a vital structure, such as, for example and without limitation, the mandibular nerve.

Because of the strength of TCA (or other suitable acids useful in the methods described herein), it is advantageous, in some aspects, that the mechanism or device (e.g., syringe) not include components that are susceptible to being dissolved by TCA (or acids having a similar or higher pK$_a$ as compared to TCA). Thus, in some aspects, a device included in a kit as described herein does not include any rubber components that would be in contact with the reservoir (and the acid compositions held within the reservoir). In further aspects, the device does not include plastic in any component that would come in contact with TCA, or includes only suitable plastics that are known to not degrade, or to degrade only minimally, when in contact with acids having a similar pK$_a$ to TCA. In some non-limiting aspects, the barrel of the device is at least partially formed from glass, which will not degrade during prolonged contact with TCA.

In some aspects, the syringe and plunger are arranged or configured such that discrete, known aliquots of the composition held within the reservoir can be dispensed. In some non-limiting aspects, stops arranged on the syringe barrel and/or the plunger shaft are provided to allow for the precise delivery of only the desired aliquot. Technology for allowing for repeated delivery of known aliquots is known, for example, repeating dispensers sold commercially by Hamilton Robotics (Reno Nev.), Restek (Bellefonte Pa.), as well as self-refilling syringes from DWK Life Sciences (Millville N.J.). In some aspects, the syringe and/or plunger are configured such that aliquots of about 0.3 ml, about 0.4 ml, about 0.5 ml, about 0.6 ml, about 0.7 ml, or about 0.8 ml (all volumes and sub-ranges therebetween inclusive) of TCA can be delivered during endodontic treatment. Those of skill in the art will appreciate that syringes/plungers can be configured to deliver other desired aliquots that would be useful in various aspects of endodontic treatment, and that such configurations fall within the scope of the invention described herein.

Figure 1:
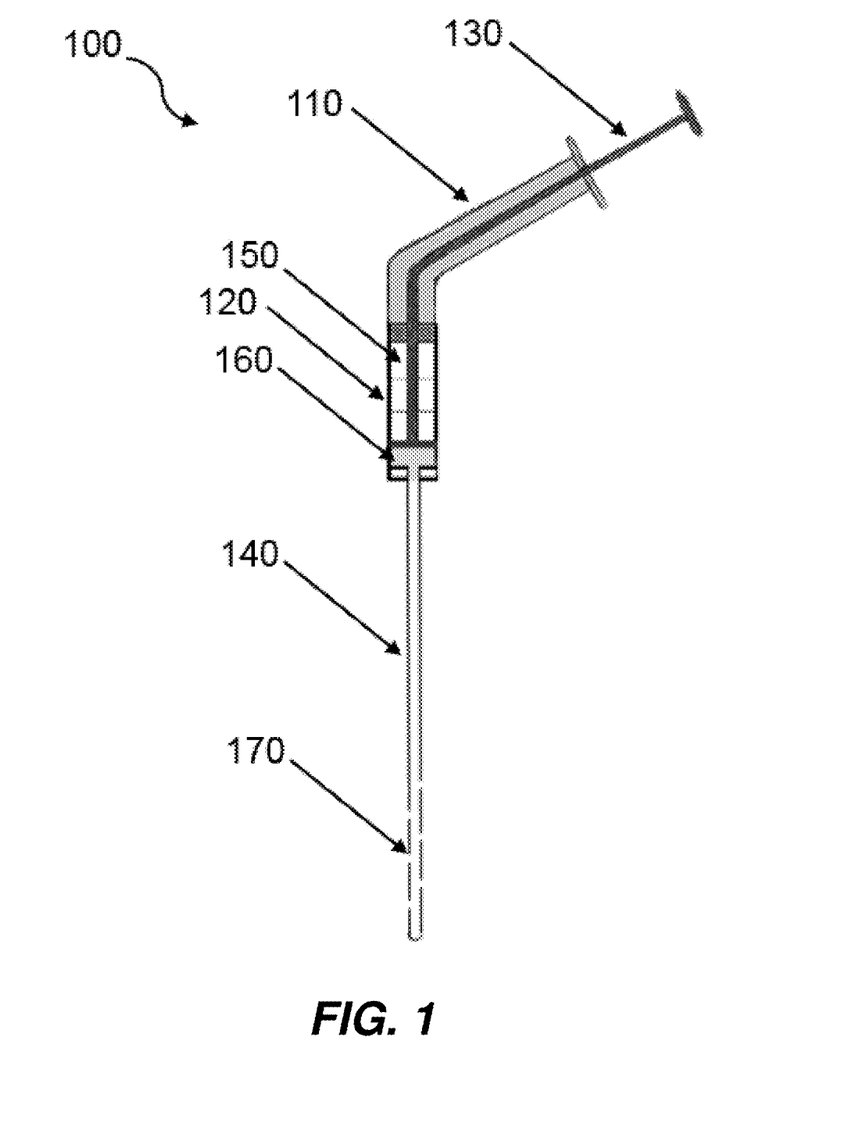
FIG. 1 is a schematic view of a device for holding and delivering a composition for endodontic debridement according to one non-limiting aspect of the present invention.
Figure 2:
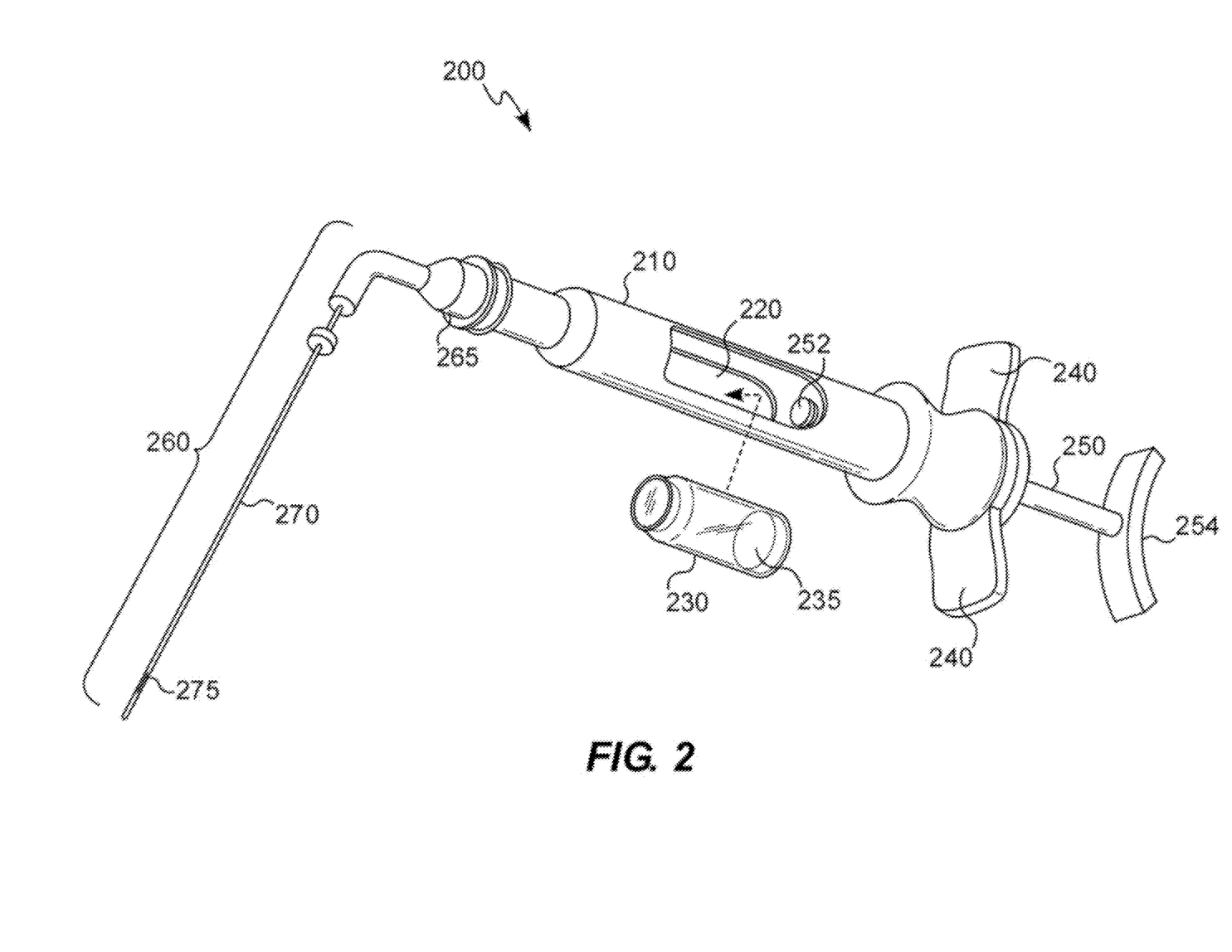
FIG. 2 is a perspective view of a device for holding and delivering a composition for endodontic debridement according to one non-limiting aspect of the present invention.
Figure 3:
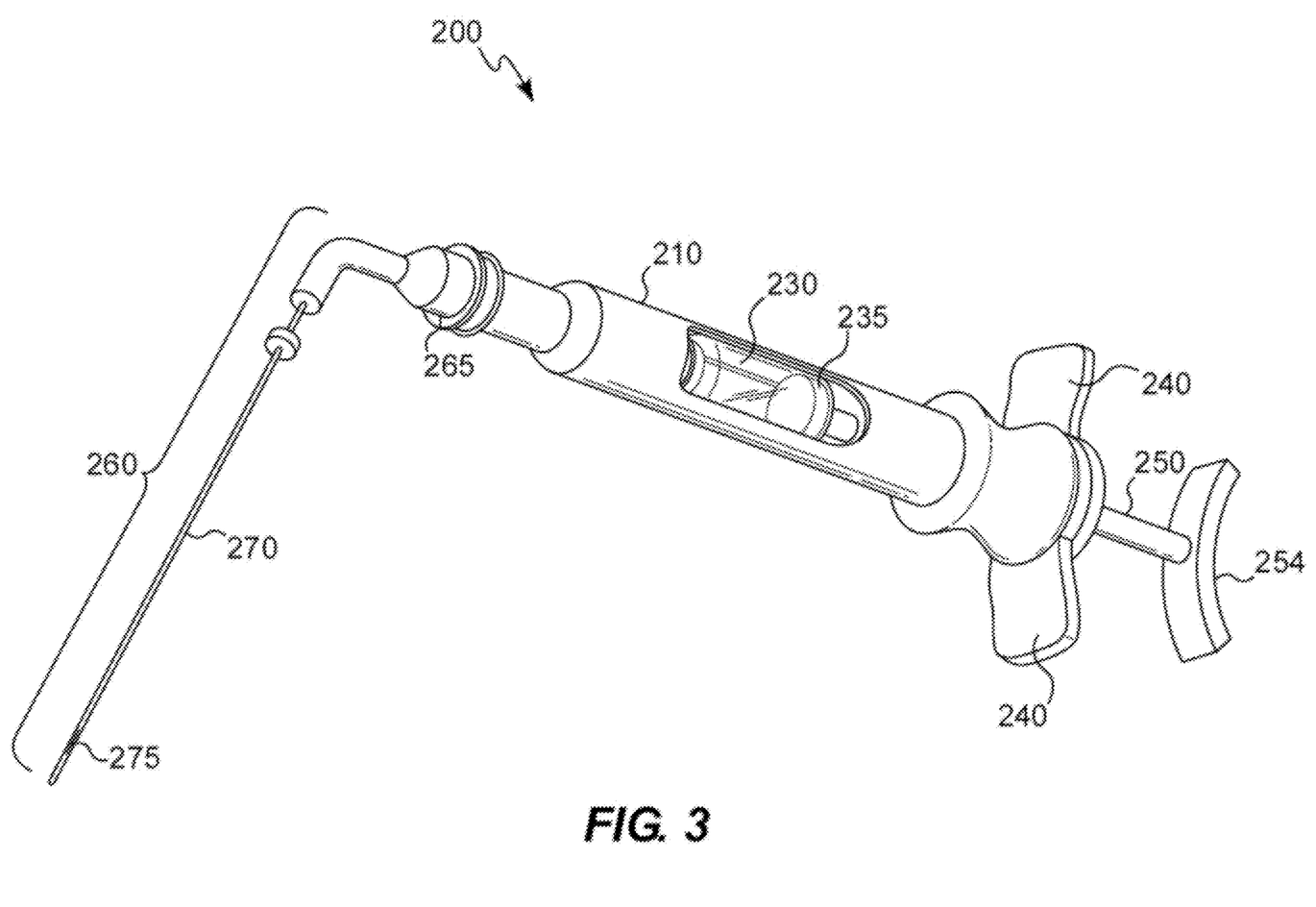
FIG. 3 is a perspective view of a device for holding and delivering a composition for endodontic debridement according to one non-limiting aspect of the present invention.
Figure 4:
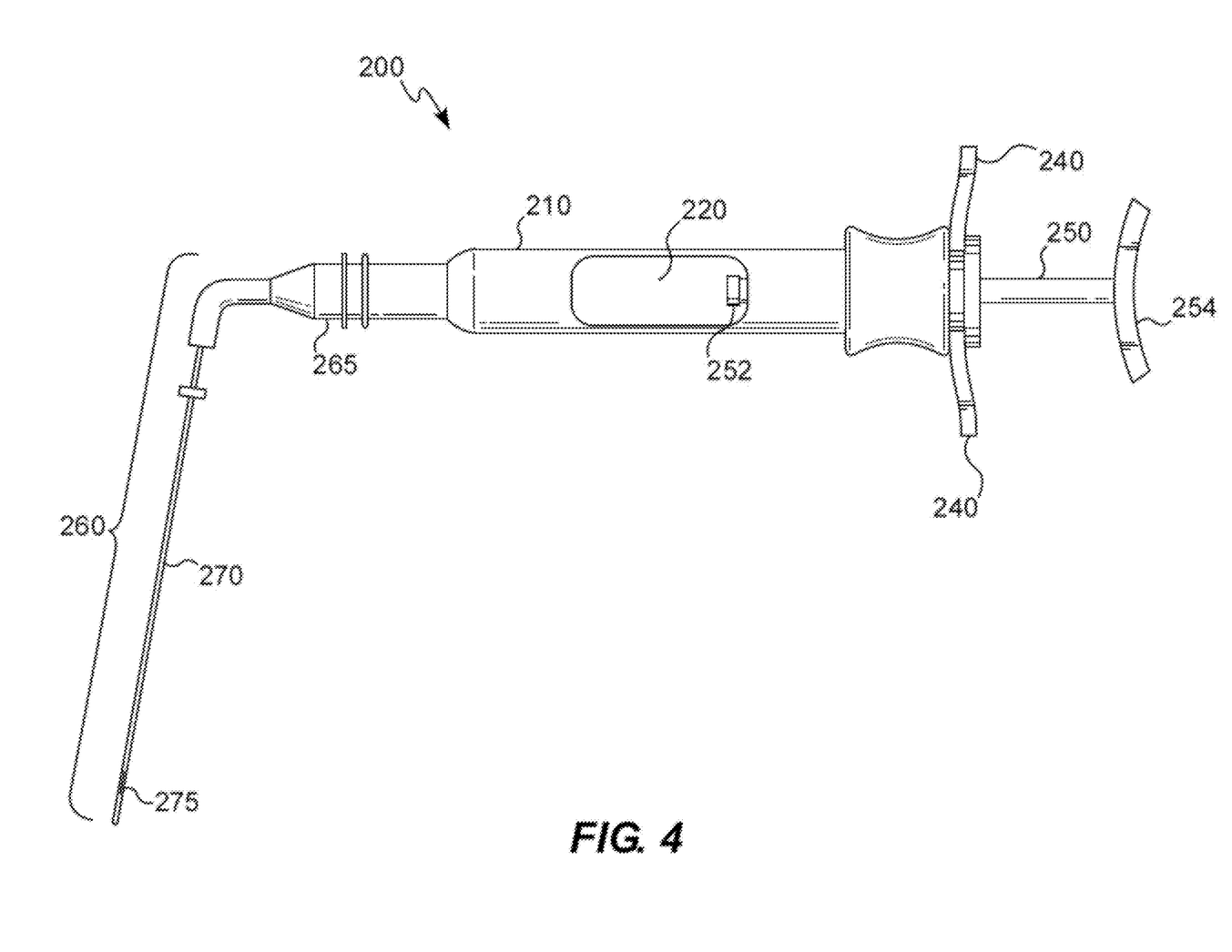
FIG. 4 is a side view of a device for holding and delivering a composition for endodontic debridement according to one non-limiting aspect of the present invention.
Figure 5:
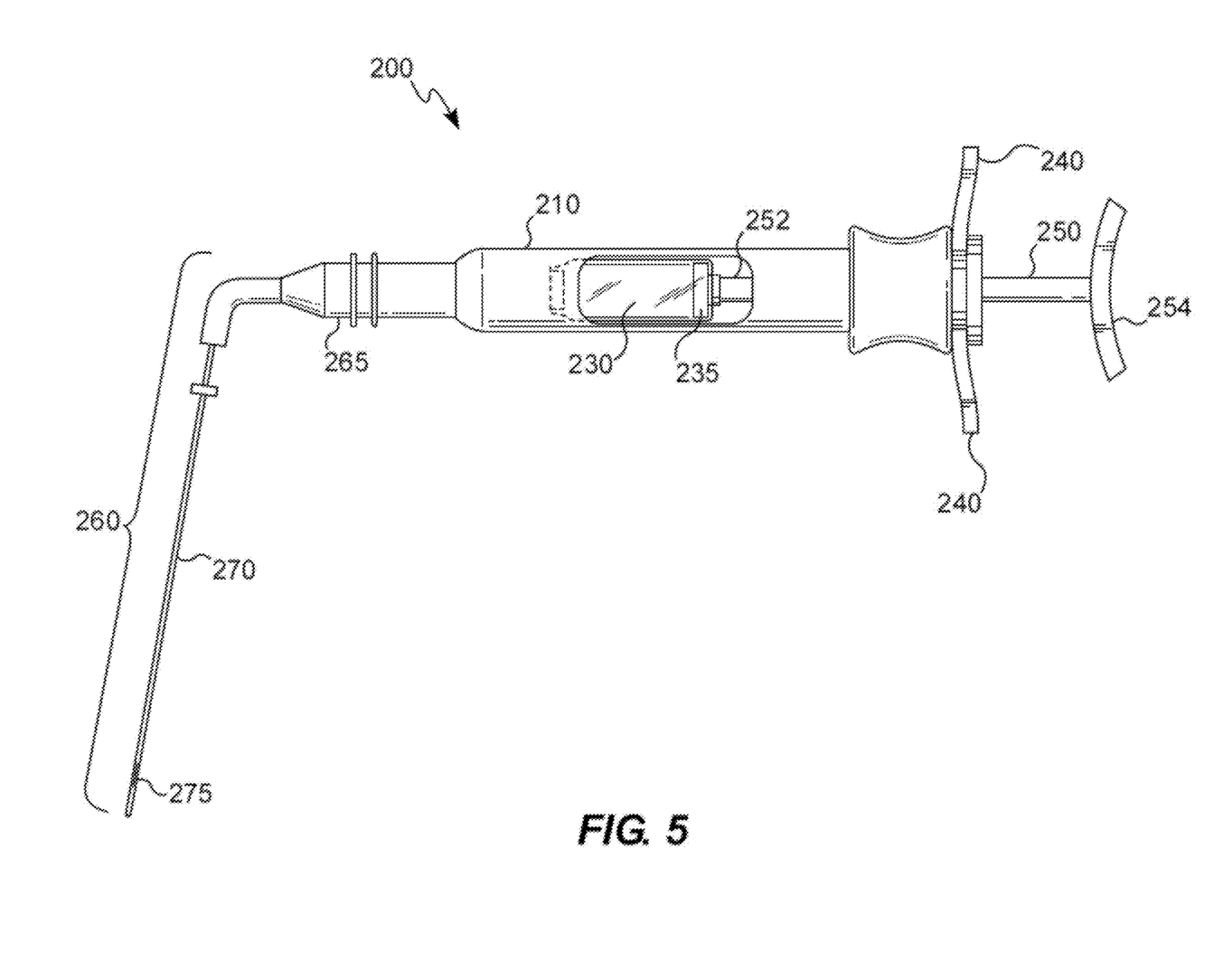
FIG. 5 is a side view of a device for holding and delivering a composition for endodontic debridement according to one non-limiting aspect of the present invention.
Figure 6:
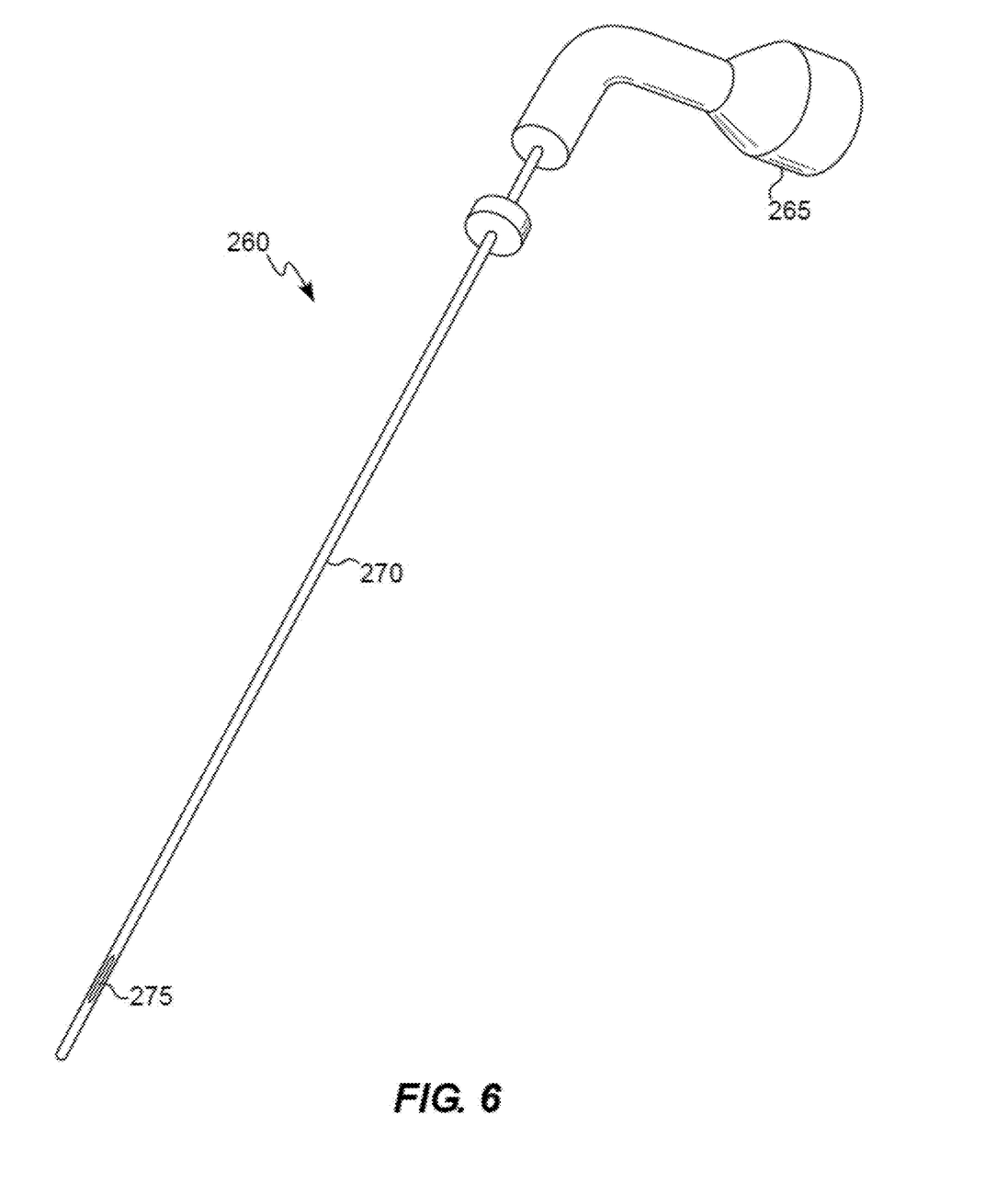
FIG. 6 is perspective view of a needle assembly of a device for holding and delivering a composition for endodontic debridement according to one non-limiting aspect of the present invention.

FIG. 1 shows a non-limiting aspect of a mechanism or device 100 suitable for delivery of TCA, or other suitable acid, during endodontic treatment as described herein. In the illustrated non-limiting aspect, the device is a syringe-like device 100 capable of holding one or more aliquots of TCA or other suitable acid. In the illustrated embodiment, device 100 includes a barrel having two portions 110, 120, a plunger 130, and a needle 140. Device 100 includes in the interior of barrel, in reservoir 150, one or more aliquots of TCA 160. As described above, the aliquots can be of any useful volume for endodontic treatment. The illustrated aspect includes a syringe barrel having an angle between portions 110 and 120 to increase access and precise delivery to the target area during endodontic treatment. As described above, in aspects the barrel can be formed of two different materials. For example, and without limitation, barrel portion 110 can be formed of plastic, or other material that is cost-effective, and that would degrade with prolonged contact with TCA 160, and barrel portion 120 can be formed of glass or other material that will not degrade, or will degrade only inconsequentially, when placed in contact with TCA 160 for extended periods of time. Similarly, needle 140 can be formed of a material that does not degrade when in contact with TCA 160. While needle 140 is shown with a blunted tip, those of skill in the art will appreciate that any useful shape could be adopted. The illustrated aspect further includes side vents 170 in the syringe needle 140 to improve delivery control.

Turning to FIGS. 2-5, shown is another non-limiting aspect of a mechanism or device 200 suitable for delivery of TCA, or other suitable acid, during endodontic treatment as described herein. In the illustrated non-limiting aspect, the device 200 is a syringe-like device capable of holding one or more aliquots of TCA or other suitable acid. While the embodiment illustrated in FIGS. 2-5 show a device with a removable or replaceable ampule 230, those of ordinary skill in the art will appreciate that a device suitable for delivery of TCA or other suitable acid can be a single use, pre-filled device. Device 200 includes a barrel 210 and, in embodiments in which the device is reusable, an opening or window 220 to allow for the insertion and removal of an ampule 230. A useful ampule 230 can include a stopper 235 on which a proximal portion 252 of plunger rod 250 can act to expel TCA or other suitable acid from the ampule 230 and through the syringe needle 270. Ampule 230, including stopper 235, can be formed of any useful material that does not corrode with prolonged contact with TCA or other acid(s) of similar strength. Device 200 includes a gripping arrangement 240, shown in FIGS. 2-5 as finger grips, to allow for the device to be manipulated for delivery of TCA to regions within a patient's mouth. Plunger 250 can include at a proximal end thereof 254 a thumb pad for actuation.

Device 200 also includes a needle 270 to allow the TCA, or other suitable acid, to be delivered to target area(s) within a patient's mouth. In the embodiment illustrated in FIGS. 2-6, needle 270 is angled with respect to a longitudinal axis of the syringe barrel 210. Those of skill in the art will appreciate that the location at which the needle is angled can vary. For example, as shown in FIGS. 2-6, needle is angled substantially at a point of connection to needle hub 265. However, in other aspects, needle 270 can be coaxial with the longitudinal axis of syringe barrel 210 for a substantial, e.g., 10%, 20%, 30%, 40%, 50%, 60%, 70%, 80%, or 90% (all ranges and values therebetween inclusive), of the length of the needle 270, and that the angle can be implemented at various regions to account for different targets within the mouth. In non-limiting aspects (not shown with respect to the aspect of FIG. 2), the needle can be straight or substantially straight, that is, coaxial with the syringe barrel 210. With continuing reference to FIGS. 2-6, device 100 includes needle 270, which can be affixed to syringe barrel 210 or can be a removable and replaceable needle assembly 260. In either aspect, a needle assembly 260 can include a needle hub 265 and needle 270. Needle hub 265 can, as described above, be permanently affixed to syringe barrel 210 or removable therefrom. Removable needle hubs can include those with luer connections to enable connection to a syringe barrel, or any other useful connection known to those of skill in the art. In non-limiting aspects, needle 270 can include one or more vents 275 in a sidewall thereof, to control delivery and, for example and without limitation, to prevent gross apical extrusion. While the vent 275 in FIGS. 2-6 is shown at a distal end of the needle (further from the syringe barrel), those of skill in the art will appreciate that the location and number of the vent(s) can be modified similar to the manner that the overall arrangement/shape of the needle can be modified, in order to, for example, accommodate different anatomies.

Also provided herein are methods of digesting root canal pulp, performing pulpectomies, and debriding wounds during endodontic treatment. The methods include delivering, administering, or otherwise contacting dental pulp with a composition including TCA, as described herein. As described above, in aspects the composition can include suitable excipient(s) or carrier(s), or, in other aspects, can consist essentially of or consist only of TCA (e.g., 90% TCA). In some aspects, the TCA is aqueous TCA.

In some aspects of methods as described herein, the TCA is aqueous and is delivered to the root canal, in some aspects the pulp chamber floor of a tooth, as an irrigation fluid. In some aspects, a syringe or other fluid-dispensing device (as described herein) is used to deliver the fluid. In other aspects, a solution including TCA (and, optionally, one or more excipient(s) or carrier(s) as described herein) is absorbed into, adsorbed on, or impregnated into a solid or semi-solid carrier as is known in the dental arts. In some aspects, the carrier is an absorbent paper, gauze, or the like that allows for placement into a desired area (e.g., the root canal, in contact with the pulp chamber floor, etc.) and simple removal from the same area.

As noted above, a shortcoming of known debridement methods is the relatively prolonged amount of time that the treatment must be used. In contrast to, for example, sodium hypochlorite (10 minutes), methods as described herein require contact between the pulp and the composition including TCA for much shorter periods of time. In some aspects, the composition described herein is placed in contact with the pulp to dehydrate and render the pulp more susceptible to dissolution by another composition, for example and without limitation, sodium hypochlorite. Without wishing to be bound by the theory, a mechanism of action of TCA in endodontic treatment is believed to include dehydration of pulp, which results in a shrinking of pulp volume, resulting in a "pulling back" of pulp from dentin walls. This change in the volume/configuration of the pulp is believed to allow for more thorough access of sodium hypochlorite to the pulp, increasing dissolution of pulp by the sodium hypochlorite. Again, without wishing to be bound by the theory, addition of sodium hypochlorite to TCA at the site of endodontic treatment is believed to produce chlorine gas and water, which results in bubbling/ foaming. The chlorine gas is believed to play an antibiotic role at the site of treatment, and the water that is produced is a harmless end product of the chemical reaction. In some aspects, the TCA is maintained in contact with the pulp for five minutes or fewer, four minutes or fewer, three minutes or fewer, two minutes or fewer, or one minute or fewer (though more than zero seconds), all times and subranges therebetween inclusive.

Also provided herein is a method of performing endodontic treatment, using a composition and, optionally, a kit as described herein. In aspects, the method includes the step of performing endodontic access to access the pulp chamber. Following access, in some aspects, coronal flaring is performed to open up at least one of the root canals. In some aspects, at this point TCA is applied to the pulp chamber floor and/or one or more of the root canals. In some aspects, with one or more appropriate dental or endodontic tools, the composition is dispersed toward the apex to promote/maintain apical patency. In some aspects, the application of TCA is followed by optional flushing or washing, optionally with sodium hypochlorite, and, optionally, additional application of sodium hypochlorite. As noted above, without wishing to be bound by the theory, it is believed that application of TCA dehydrates pulp, rendering the pulp more susceptible to thorough dissolution by sodium hypochlorite. Further, as the reaction of TCA and sodium hypochlorite results in production of water, in some aspects it is not necessary to perform a separate flushing/washing step (however, in aspects, the water that is produced through the reaction of TCA and sodium hypochlorite is washed/flushed from the site of treatment, and fresh sodium hypochlorite is applied). In some aspects, these steps (applying TCA and, optionally, dispersing the same) are performed one or more times. In some aspects, the steps of applying TCA and washing/flushing, optionally with sodium hypochlorite, followed by optional additional application of sodium hypochlorite) are repeated one or more times until the pulp has been dissolved. In some aspects, as described above, the composition including TCA is maintained in contact with the pulp for five minutes or fewer, four minutes or fewer, three minutes or fewer, two minutes or fewer, or one minute or fewer (though more than zero seconds) per application, all times and subranges therebetween inclusive Thereafter, the root canals are cleaned and shaped according to methods known to those of skill in the art. Following root canal cleaning/shaping, in some aspects, a composition including TCA is introduced to the root canal, in some aspects, with a solid or semi-solid carrier, such as an absorbent paper or gauze, to further dehydrate any possible remaining unwanted tissue, followed by application of sodium hypochlorite. Thereafter, the root canal is flushed to remove the TCA and/or sodium hypochlorite and prepare the root for filling. As noted above, as the reaction of TCA and sodium hypochlorite results in production of water, in some aspects it is not necessary to perform a washing step. In some aspects the root canal is flushed with one, two, three, four, or more different flushing solutions. Flushing solutions are known to those of skill in the art, and include, without limitations, sodium hypochlorite, EDTA, chlorhexidine, alcohol, and chloroform. In some aspects, the flushing solutions are one or more of sodium hypochlorite, EDTA (e.g., 17% EDTA), and one or more alcohols. In some aspects, the flushing solutions are introduced (and removed) in a specific order: sodium hypochlorite, alcohol, EDTA, and alcohol. In non-limiting aspects, the alcohol utilized for a final flush is isopropanol, ethyl alcohol, and/or absolute alcohol. Thereafter, the root canal is dried, optionally with paper points, and filled as is known in the art (e.g., with gutta-percha).

Figure 7:
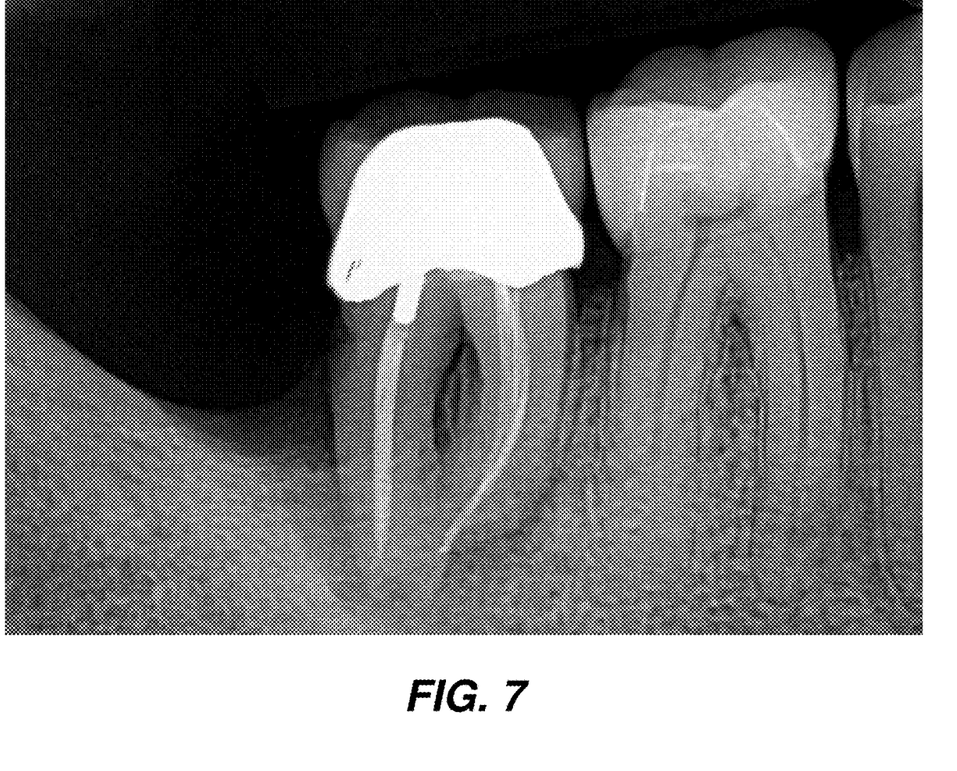
FIG. 7 is a radiograph of a tooth on which endodontic treatment was performed without a composition according to one non-limiting aspect of the present invention.
Figure 8:
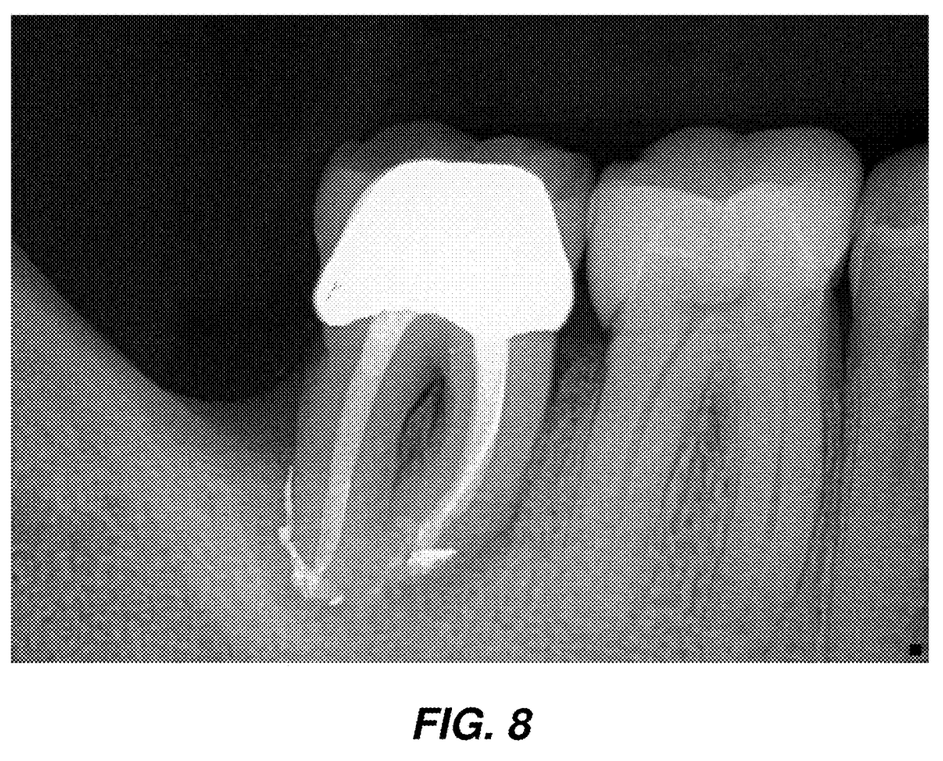
FIG. 8 is a radiograph of a tooth on which endodontic treatment was performed with a composition according to one non-limiting aspect of the present invention.

In non-limiting aspects, a protocol for performing endodontic access includes performing endodontic access to access the pulp chamber. Following access, in some aspects, coronal flaring is performed to open up at least one of the root canals. In some aspects, at this point TCA is applied to the pulp chamber floor and/or one or more of the root canals. In some aspects, with one or more appropriate dental or endodontic tools, the composition is dispersed toward the apex to promote/maintain apical patency. In some aspects, the application of TCA is followed by flushing with sodium hypochlorite. In embodiments or aspects in which endodontic treatment requires or would benefit from more than one visit (e.g., in the case of necrotic pulp), a temporary sealing material and/or temporary filling material, for example those described below, for example calcium hydroxide, can be applied to the canal. Then, at a subsequent visit, TCA can be used to dissolve and/or remove the temporary sealing material and/or temporary filling material. Thereafter, in aspects, the root canals are optionally flushed and are then cleaned and shaped according to methods known to those of skill in the art. Following root canal cleaning/shaping, the root canal is flushed with EDTA to prepare the root for filling. In aspects, following flushing with EDTA, the root canal is flushed with an alcohol (isopropanol, ethyl alcohol, and/or absolute alcohol). Thereafter, the root canal is dried, optionally with paper points, and filled as is known in the art Experiments with TCA show that the use of such compositions provides improved access of a debridement composition to microscopic root canal branches, fins, and anastomoses. More specifically, use of TCA in endodontic treatment including sodium hypochlorite results in a cleaner apex, lessened bleeding or elimination of bleeding altogether, reduced pain (for example as shown below in the Example), particularly in lower molar cases, and less inflammation (again, particularly in lower molar cases). These features, for example increased access and a cleaner apex, result in a far cleaner root canal, removal of smaller amounts of dentin during the endodontic treatment, and superior healing and success of the endodontic treatment. FIGS. 7 and 8 show radiographic images from prior to (FIG. 7) and following (FIG. 8) endodontic treatment with a TCA composition as described herein. The image in FIG. 7 is of a tooth that had previously undergone endodontic treatment, but without TCA as a debridement solution. As can be seen, the tooth in FIG. 7 shows a poorly-cleaned root with low density and an absence of irregular deformation (also known as corkage). In contrast, as shown in FIG. 8, after endodontic treatment with TCA, the retreated root shows a thicker irregular deformed material that fully fills the root tip.

Another notable effect of treatment with TCA is improved removal of debris, such as dentin debris, as well as material from prior endodontic treatment, either during retreatment cases, or temporary sealing and/or filling material from prior preparatory visits, for example where endodontic treatment may require several visits to complete (e.g., in the case of necrotic pulp).

For example, when endodontic treatment may require several visits, an approach can be to fill the canal with an intracanal medicament, a sealing material, and/or a filling material, such as calcium hydroxide, mineral trioxide aggregate, zinc oxide eugenol, glass ionomers, various plastics (e.g., thermoplastic polyesters), rubbers (natural and/or synthetic), dentin (e.g., hydroxyapatite crystalline debris), resins (e.g., methacrylate-based resins), tricalcium silicate, and ceramics (e.g., bioceramics including those containing alumina, zirconia, bioactive glass, glass ceramics, hydroxyapatite, and/or calcium phosphates). In non-limiting embodiments or aspects, the intracanal medicament, sealing material, and/or filling material is sodium hydroxide, which is a bacteriostatic material that alters the pH of the environment into which it is placed to deter bacterial growth. In non-limiting embodiments or aspects, the intracanal medicament, sealing material, and/or filling material is softened, removed, and/or dissolved by application of TCA, as described herein, to the medicament and/or material. In non-limiting embodiments or aspects, the TCA is applied to the medicament and/or material for not more than five minutes, preferably not more than four minutes, preferably not more than three minutes, most preferably not more than two minutes.

In addition, in terms of retreatment, typically the standard in the field is to use chloroform to remove prior materials, such as gutta-percha, various plastics (e.g., thermoplastic polyesters), mineral trioxide aggregate, calcium hydroxide, zinc oxide eugenol, glass ionomers, rubbers (natural and/or synthetic), dentin (e.g., hydroxyapatite crystalline debris), resins (such as those described above), tricalcium silicate, and ceramics (such as those described above). However, chloroform use can be associated with undesirable side effects, such as necrosis at the site of treatment. Trichloroacetic acid represents an optional approach during retreatment cases. Accordingly, in non-limiting embodiments or aspects, provided herein is a method of performing endodontic retreatment, including the steps of performing endodontic retreatment to access the prior sealing and/or filling material, such as those described above. Following access, in some aspects, coronal flaring is performed to open up at least one of the root canals. In some aspects, TCA is applied to the prior filling material. In other aspects, TCA is applied after treatment of the prior filling material with chloroform. In some aspects, these steps (applying TCA (optionally after application of chloroform) and dispersing the same) are repeated one or more times until the prior material has been dissolved. In some aspects, after access, chloroform is applied to the prior filling material, followed by a washing/drying with alcohol (useful alcohols are described herein), then application of TCA.

Thereafter, the root canal(s), if present, can be cleaned and shaped according to methods known to those of skill in the art. Following root canal cleaning/shaping, in some aspects, a composition including TCA is introduced to the root canal, in some aspects, with a solid or semi-solid carrier, such as an absorbent paper or gauze, to further dissolve any possible remaining unwanted tissue or material. Thereafter, the root canal is flushed to remove the TCA and prepare the root for filling. In some aspects the root canal is flushed with one, two, three, four, or more different flushing solutions. Flushing solutions are known to those of skill in the art, and include, without limitations, sodium hypochlorite, EDTA, chlorhexidine, alcohol, and chloroform. In some aspects, the flushing solutions are one or more of sodium hypochlorite, EDTA (e.g., 17% EDTA), and one or more alcohols, as described above. In some aspects, the flushing solutions are introduced (and removed) in a specific order: sodium hypochlorite, alcohol, EDTA, and alcohol. Thereafter, the root canal is dried and filled as described above.

Example

Use of TCA during endodontic treatment is associated with decreased incidence of pain following endodontic treatment. Without wishing to be bound by the theory, it is believed that the TCA composition eliminates unmyelinated C fibers in the apical pulp, particularly in mandibular molars. To assess the decreased pain, individuals were asked to provide a self-assessment, on a scale of 1-10, of pain prior to endodontic treatment, and 6, 24, 48, and 120 hours following endodontic treatment. Patients were divided into two groups, one group (Control, N=9) receiving standard endodontic treatment including sodium hypochlorite as the primary irrigant, with occasional (as necessary) flushes with 17% EDTA, and one group (Experimental, N=10) receiving endodontic treatment including the composition described herein as a pre-treatment applied to pulp to facilitate navigating calcified canals and after initial shaping with patency. The experimental group received sodium hypochlorite irrigation and, as necessary, EDTA flushing, as in the control group. Results are shown in Table 1 below.

TABLE 1

|  | Before | 6 hours | 24 hours | 48 hours | 120 hours |
| --- | --- | --- | --- | --- | --- |
| Control | 2.67 | 1 | 0.89 | 1.44 | 0.56 |
| Experimental | 3.1 | 0.7 | 0.5 | 0.4 | 0.2 |

As can be seen, use of the composition described herein reduced subjective levels of pain following endodontic treatment compared to the current "gold standard" control, sodium hypochlorite.

A more granular review of the data shows that the composition described herein is particularly useful in reducing pain in patients presenting with necrosis at the time of treatment. Patients presenting with necrosis self-reported a pain level of 4.5 before treatment, and pain levels of 0.5, 0.25, 0, and 0 at 6, 24, 48, and 120 hours following treatment, respectively.

The following clauses are illustrative of the various aspects of the present invention:

Clause 1: A method of dehydrating root canal pulp comprising administering, to dental pulp within the mouth of a patient, a composition comprising trichloroacetic acid (TCA), the composition optionally including one or more buffers or excipients.

Clause 2: The method of clause 1, wherein the composition consists essentially of TCA.

Clause 3: The method of clause 1, wherein the composition consists of TCA.

Clause 4: The method of clause 1, wherein the composition consists of 90% TCA.

Clause 5: The method of any of clauses 1-4, further comprising a step of administering sodium hypochlorite to the pulp until all the pulp has been dissolved, wherein the TCA is applied for not more than five minutes, preferably not more than four minutes, preferably not more than three minutes, most preferably not more than two minutes.

Clause 6: The method of any of clauses 1-5, wherein the composition comprising TCA is applied as an irrigation fluid.

Clause 7: The method of any of clauses 1-5, wherein the composition comprising TCA is absorbed or impregnated in a carrier, and the carrier is applied to the dental pulp.

Clause 8: The method of clause 7, wherein the carrier is an absorbent paper, gauze, or other absorbent material that can hold the composition.

Clause 9: A method of debriding a wound during endodontic treatment, comprising applying TCA to the pulp chamber floor within a root canal within the mouth of a patient.

Clause 10: The method of clause 9, wherein the composition consists essentially of TCA.

Clause 11: The method of clause 9, wherein the composition consists of TCA.

Clause 12: The method of clause 9, wherein the composition consists of 90% aqueous TCA.

Clause 13: The method of any of clauses 9-12, further comprising a step of administering sodium hypochlorite to the pulp chamber floor until all pulp has been dissolved, wherein the TCA is applied for not more than five minutes, preferably not more than four minutes, preferably not more than three minutes, most preferably not more than two minutes.

Clause 14: The method of any of clauses 9-13, wherein the composition comprising TCA is applied as an irrigation fluid.

Clause 15: The method of any of clauses 9-13, wherein the composition comprising TCA is absorbed or impregnated in a carrier, and the carrier is applied to the pulp chamber floor.

Clause 16: The method of clause 15, wherein the carrier is an absorbent paper, gauze, or other absorbent material that can hold the composition.

Clause 17: A method of performing endodontic treatment, comprising: a. performing endodontic access; b. performing coronal flaring, thereby opening one or more root canals and exposing dental pulp within the one or more canals; c. applying a composition comprising TCA to the exposed dental pulp, the composition optionally including one or more buffers or excipients; d. applying a composition comprising sodium hypochlorite to the exposed dental pulp; e. cleaning and shaping the one or more root canals; f. optionally applying a composition comprising TCA, the composition optionally including one or more buffers or excipients, to the one or more cleaned and shaped root canals; g. flushing the one or more root canals with a first flushing solution; and h. drying the one or more root canals, optionally with one or more paper points.

Clause 18: The method of clause 17, further comprising, after applying the composition comprising TCA to the exposed dental pulp, a step of dispersing the composition toward an apex of the one or more root canals.

Clause 19: The method of clause 17 or clause 18, further comprising repeating the steps of applying the composition comprising TCA to the exposed dental pulp and dispersing the composition one or more times, preferably until apical patency is established.

Clause 20: The method of any of clauses 17-19, further comprising, after flushing the one or more root canals with a first flushing solution, flushing the one or more root canals with a second flushing solution.

Clause 21: The method of clause 20, further comprising, after flushing the one or more root canals with a second flushing solution, flushing the one or more root canals with a third flushing solution.

Clause 22: The method of clause 21, further comprising, after flushing the one or more root canals with a third flushing solution, flushing the one or more root canals with a fourth flushing solution.

Clause 23: The method of any of clauses 17-22, wherein the first flushing solution comprises sodium hypochlorite.

Clause 24: The method of any of clauses 20-23, wherein the second flushing solution comprises an alcohol.

Clause 25: The method of any of clauses 21-24, wherein the third flushing solution comprises EDTA, preferably 17% EDTA.

Clause 26: The method of any of clauses 22-25, wherein the fourth flushing solution comprises an alcohol, optionally isopropyl alcohol, ethyl alcohol, and/or absolute alcohol.

Clause 27: The method of any of clauses 17-26, wherein the composition comprising TCA consists essentially of TCA Clause 28: The method of any of clauses 17-26, wherein the composition comprising TCA consists of 90% TCA.

Clause 29: The method of any of clauses 17-28, wherein step c. is performed for more than five minutes, preferably not more than four minutes, preferably not more than three minutes, most preferably not more than two minutes for at least one minute.

Clause 30: The method of any of clauses 17-29, wherein in step c. the composition comprising TCA is applied to the dental pulp as an irrigation fluid.

Clause 31: The method of any of clauses 17-30, wherein in step f. the composition comprising TCA is applied to the cleaned and shaped one or more root canals with a carrier.

Clause 32: The method of clause 31, wherein the carrier is an absorbent paper, gauze, or other absorbent material that is configured to hold a quantity of the composition.

Clause 33: A kit comprising: a syringe comprising: a barrel comprising a proximal end, a distal end, and a sidewall therebetween defining a reservoir; a plunger received at least partially within the reservoir; and a metal needle tip attached to the distal end of the syringe barrel, and a composition comprising TCA, optionally provided in an ampule, and optionally including one or more buffers or excipients, received within the reservoir.

Clause 34: The kit of clause 33, wherein the barrel is configured such that no rubber material and/or no corrosion-susceptible plastic material contacts the composition held within the reservoir.

Clause 35: The kit of clause 33 or clause 34, wherein the composition consists essentially of TCA.

Clause 36: The kit of clause 33 or clause 34, wherein the composition consists of 90% TCA.

Clause 37: The kit of any of clauses 33-36, wherein the needle is a 30-gauge needle.

Clause 38: The kit of any of clauses 33-37, wherein the syringe barrel and/or are configured to deliver aliquots of the composition when the plunger is depressed.

Clause 39: The kit of clause 38, wherein the volume of the aliquot is approximately 0.5 ml.

Clause 40: The kit of any of clauses 33-39, wherein the syringe barrel or ampule is formed of glass or a corrosion-resistant plastic.

Clause 41: The kit of any of clauses 33-40, wherein the syringe is angled.

Clause 42: The kit of any of clauses 33-41, wherein the needle is angled.

Clause 43: The kit of any of clauses 33-42, wherein the needle is about 10 mm to about 15 mm in length.

Clause 44: The kit of any of clauses 33-43, wherein the kit further comprises sodium hypochlorite, optionally in an ampule, and, optionally, EDTA and an alcohol, optionally isopropanol, ethyl alcohol, and/or absolute alcohol, optionally wherein the EDTA and/or the alcohol are provided in ampules configured to be used with the syringe.

Clause 45: A method of performing a dental pulpectomy comprising applying a composition comprising TCA, and optionally one or more buffers or excipients, to dental pulp within a root canal within the mouth of a patient.

Clause 46: The method of clause 45, wherein the composition consists essentially of TCA.

Clause 47: The method of clause 45, wherein the composition consists of TCA.

Clause 48: The method of clause 45, wherein the composition consists of 90% aqueous TCA.

Clause 49: The method of any of clauses 45-48, wherein the composition is applied to the dental pulp t for not more than five minutes, preferably not more than four minutes, preferably not more than three minutes, most preferably not more than two minutes.

Clause 50: The method of any of clauses 45-49, wherein the composition is applied as an irrigation fluid.

Clause 51: The method of any of clauses 45-49, wherein the composition is absorbed or impregnated in a carrier, and the carrier is applied to the dental pulp.

Clause 52: The method of clause 51, wherein the carrier is an absorbent paper, gauze, or other absorbent material that can hold the composition.

Clause 53: The method of any of clauses 45-52, wherein the method further comprises applying sodium hypochlorite, optionally after washing or flushing the composition comprising TCA.

Although the invention has been described in detail for the purpose of illustration based on what is currently considered to be the most practical aspects, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method of removing a medicament, a sealing material, and/or a filling material from a root canal, comprising applying to the medicament, sealing material, and/or filling material a composition comprising trichloroacetic acid (TCA).

2. The method of claim 1, wherein the composition consists essentially of TCA.

3. The method of claim 1, wherein the composition consists of 90% TCA.

4. The method of claim 1, wherein the composition is applied to the filling material for no longer than five minutes.

5. The method of claim 1, wherein the medicament, sealing material, and/or filling material comprises calcium hydroxide.

6. The method of claim 1, wherein the medicament, sealing material, and/or filling material is one or more selected from the group consisting of rubber, gutta percha, plastic, hydroxyl apatite, resin, tricalcium silicate, and a bioceramic.

7. A method of performing endodontic treatment, comprising:

a. performing endodontic access;
b. performing coronal flaring, thereby opening one or more root canals and exposing dental pulp within the one or more canals;
c. applying a composition comprising trichloroacetic acid (TCA) to the exposed dental pulp;
d. applying a composition comprising sodium hypochlorite to the exposed dental pulp;
e. applying a medicament, sealing material, and/or filling material to the one or more root canals;
f. applying a composition comprising TCA to the medicament, sealing material, and/or filling material;
g. cleaning and shaping the one or more root canals;
h. flushing the one or more root canals with a first flushing solution; and
i. drying the one or more root canals.

8. The method of claim 7, further comprising, after applying the composition comprising TCA to the exposed dental pulp, a step of dispersing the composition comprising TCA toward an apex of the one or more root canals.

9. The method of claim 8, further comprising repeating the steps of applying the composition comprising TCA to the exposed dental pulp, dispersing the composition comprising TCA, and applying the composition comprising sodium hypochlorite to the exposed dental pulp one or more times, until apical patency is established.

10. The method of claim 7, further comprising, after flushing the one or more root canals with the first flushing solution, flushing the one or more root canals with a second flushing solution comprising an alcohol.

11. The method of claim 10, further comprising, after flushing the one or more root canals with the second flushing solution, flushing the one or more root canals with a third flushing solution comprising EDTA.

12. The method of claim 11, further comprising, after flushing the one or more root canals with the third flushing solution, flushing the one or more root canals with a fourth flushing solution comprising an alcohol.

13. The method of claim 7, wherein step h. comprises flushing the one or more root canals with EDTA and then flushing the one or more root canals with an alcohol.

14. The method of claim 7, wherein the composition comprising TCA consists essentially of TCA.

15. The method of claim 7, wherein the composition comprising TCA consists of 90% aqueous TCA.

16. The method of claim 7, wherein step c. is performed for not more than five minutes.

17. The method of claim 7, wherein step f. is performed for not more than five minutes.

18. The method of claim 7, wherein the medicament, sealing material, and/or filling material comprises calcium hydroxide.

19. A method of removing dentin debris from a root canal, comprising applying a composition comprising trichloroacetic acid (TCA) to the dentin debris.

20. The method of claim 19, wherein the composition comprising TCA consists of 90% aqueous TCA.

* * * * *